United States Patent [19]
Wormald et al.

[11] Patent Number: 4,785,175
[45] Date of Patent: Nov. 15, 1988

[54] INSPECTION OF BURIED PIPELINES

[75] Inventors: Malcolm R. Wormald, Abingdon; Lionel G. Sanders, Berick Salome; Colin G. Clayton, Shippon, all of United Kingdom

[73] Assignee: British Gas plc, London, United Kingdom

[21] Appl. No.: 45,205

[22] Filed: May 4, 1987

Related U.S. Application Data

[63] Continuation of Ser. No. 676,256, Nov. 29, 1984.

[30] Foreign Application Priority Data

Nov. 30, 1983 [GB] United Kingdom ............... 8331914

[51] Int. Cl.⁴ .......................................... G01V 5/10
[52] U.S. Cl. ............................. 250/360.1; 250/253; 250/266; 250/358.1
[58] Field of Search ............ 250/360.1, 359.1, 358.1, 250/267, 266, 265, 253, 269

[56] References Cited

U.S. PATENT DOCUMENTS

| 2,398,324 | 4/1946 | Pontecorvo | 166/253 |
| 2,940,302 | 6/1960 | Scherbatskoy | 318/583 |
| 2,997,586 | 8/1961 | Scherbatskoy | 378/89 |
| 3,060,315 | 10/1962 | Scherbatskoy | 250/303 |
| 3,202,822 | 8/1965 | Kehler | 250/266 |
| 3,546,456 | 12/1970 | Grice | 250/253 |
| 4,146,791 | 3/1979 | Dahl et al. | 378/59 |

FOREIGN PATENT DOCUMENTS

| 1248397 | 9/1971 | United Kingdom . |
| 1296320 | 11/1972 | United Kingdom . |
| 1306535 | 2/1973 | United Kingdom . |
| 1362580 | 8/1974 | United Kingdom . |
| 2039366 | 8/1980 | United Kingdom . |
| 2062217 | 5/1981 | United Kingdom . |
| 2087072 | 5/1982 | United Kingdom . |
| 2098300 | 11/1982 | United Kingdom . |
| 2102565 | 2/1983 | United Kingdom . |
| 2109926 | 6/1983 | United Kingdom . |
| 2113387 | 8/1983 | United Kingdom . |

Primary Examiner—Janice A. Howell
Assistant Examiner—Constantine Hannaher
Attorney, Agent, or Firm—William R. Hinds

[57] ABSTRACT

A method of inspecting the cover of a buried pipeline comprising the operations of irradiating the inner wall of the pipeline with neutrons from a radioactive source carried by a vehicle traversing the pipeline, measuring the intensity of ionizing radiation within the pipeline arising from nuclear interactions occuring within the cover of the pipeline and its surroundings due to the neutrons emitted by the source, and recording the measured intensity of the said ionising radiation together with data representative of the position of the vehicle along the pipeline. Apparatus for carrying out the method also is described.

11 Claims, 5 Drawing Sheets

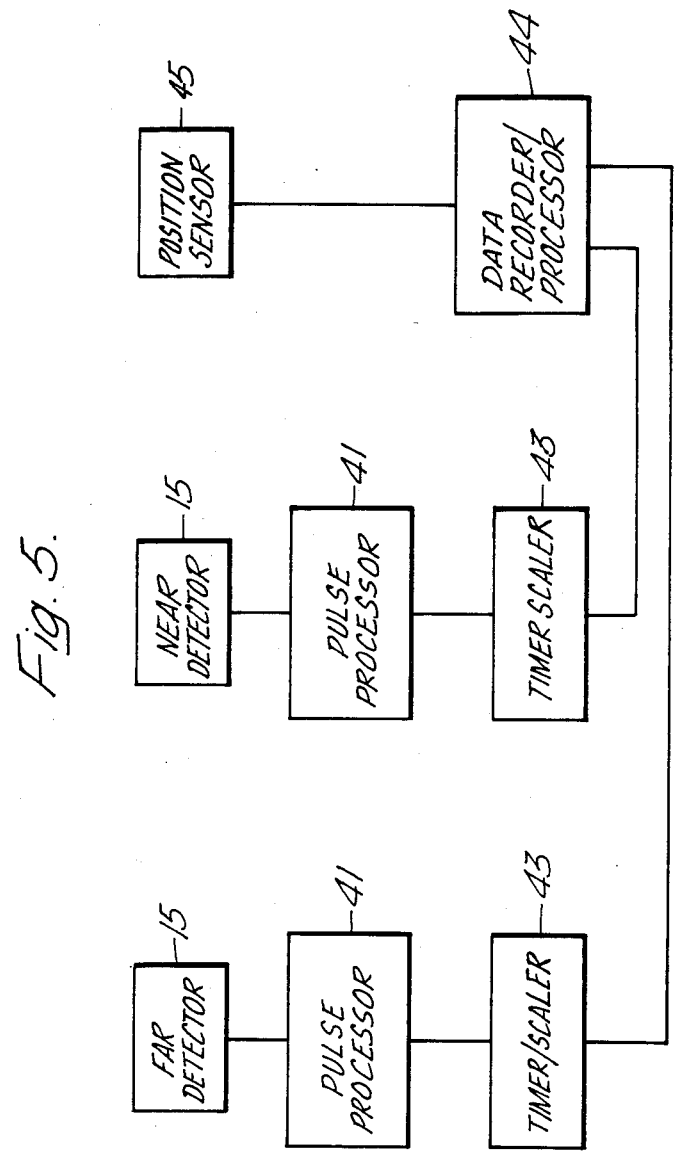

INSPECTION OF BURIED PIPELINES

This application is a continuation of application Ser. No. 676,256, filed Nov. 29, 1984.

The present invention relates to the inspection of buried pipelines to determine the integrity or nature of the cover of such pipelines.

In order to protect marine pipelines from the corrosive action of sea water, and possible damage from ships' anchors, such pipelines generally are coated with bitumen and concrete and buried in the sea bed with a good base so as to avoid excessive strains on the pipeline. However, the motion of the sea may cause the seabed material to be removed or fluidised with the result that the pipeline may be exposed or its support may be removed, so making it susceptible to vortex shedding induced vibration. External damage or erosion may remove some of the concrete or bitumen so allowing parts of the pipeline to become buoyant as well as being exposed to accelerated corrosion. Any resulting damage to the pipeline is very expensive to repair, is likely to lead to a serious loss of production, and in the case of an oil pipeline, to extensive pollution of the sea.

It is therefore of the utmost importance that the integrity or nature of the cover, that is to say the coating, burial layer, and support of such pipelines should be inspected from time to time so that remedial action can be taken in good time should it prove to be necessary. At present such inspections are carried out visually and/or by means of sidescan sonar from submersibles which track along the length of the pipe and operate from surface vessels. In less arduous situations, divers are used. Such methods can be operated satisfactorily only in reasonable weather conditions when both the sea state and the turbidity of the water are low.

A method of testing the integrity of the cover of buried pipelines is disclosed in the specification of UK Patent No. 1,563,540 (corresponding to U.S. Pat. No. 4,146,791 in which the intensity of nuclear ionising radiations arising from nuclear reactions occurring naturally in the material surrounding the pipeline and penetrating the wall of the pipeline is measured by an instrumented vehicle which travels through the pipeline. In one aspect of the invention disclosed in UK Specification No. 1,563,540, the measured γ-ray intensity spectrum is compared with one taken on a previous occasion and any differences are detected and noted. In a second aspect, a number of detectors are disposed symmetrically about the axis of the vehicle, and their outputs are compared with one another. Any large difference indicates a similar difference in the pipeline cover.

The methods of inspection described in UK Specification No. 1,563,540 suffer from the defects that they both rely on the uniform distribution of naturally occurring radioactive materials in the pipeline cover, which may not occur in practice. Also the naturally occurring γ-rays have relatively low energies and they are attenuated considerably by the concrete part of the pipeline cover. Furthermore, the first method requires the storage of a large amount of data, which reduces the length of pipeline which can be inspected at any one time.

According to the invention, in a method of determining the integrity of material in covering or supporting relationship with a buried pipeline from recorded data obtained from a single run of a pig through the pipeline, the pig comprising source means which emits output radiation, the run of the pig causes interactions between the output radiation and the material all around the pipeline, which interactions produce ionizing radiation directed toward the pig, the pig further comprising shield material, a longitudinal axis, and detectors arranged around the axis and producing first data in response to the ionizing radiation, the detectors being shielded by the shield material so that each of the detectors responds primarily to the ionizing radiation from those of the interactions arising anywhere in a respective one of a number of view fields each extending part way around the pipeline, the first data from each detector being representative of the ionizing radiation from the interactions in the respective field, the method further comprising, as the pig advances through the pipeline, recording in one pig for each detector respective data to produce the recorded data, and recording in the pig second data representative of the position of the pig along the pipeline.

Preferably, successive ratios indicative for each said respective view field of the presence or absence of said material are formed from parts of successive energy spectra of the ionizing radiation.

Also according to the invention, a pipeline pig for use in determining the integrity of material in covering or supporting relationship with a buried pipeline has a central longitudinal axis and comprises source means to emit output radiation having interactions with the material all around the pipeline, which interactions produce ionizing radiation directed toward the pig, the pig further comprising shield material and detectors arranged around the axis and producing first data in response to the ionizing radiation, the shield material being arranged to shield the detectors from direct irradiation by the output radiation, the shield material being arranged to ensure that each of the detectors responds primarily to the ionizing radiation from those of the interactions arising anywhere in a respective one of a number of view fields each extending part way around the pipeline, the first data from each detector being representative of the ionizing radiation from the interactions in the respective view, the pig further comprising means which produces second data representative of the position of the pig along the pipeline, and recorder means which records the first and second data.

The concrete coating which in normal conditions surrounds the buried pipeline attenuates both outgoing and incoming radiations. The presence or absence of the concrete coating is indicated by changes in the intensity of γ-rays within the pipeline due to neutron capture by hydrogen in the medium outside the pipeline. In the absence of the concrete, this is increased due to the increase in the hydrogen content of the medium immediately surrounding the pipeline. On the other hand, the intensity of high-energy γ-rays generated by the capture of neutrons in the concrete coating and the iron pipe wall pipeline is higher when the concrete coating is present and decreases in its absence, again due to increased neutron capture in the hydrogenous medium outside the pipeline.

In any of the aspects of the invention, the data, which is recorded may be either γ-ray spectra, or neutron, absorption spectra, and can be taken regularly over fixed increments of distance along the pipeline, or of time, or by another marker criterion, for example every pipeline section, or submultiple of this, as indicated by the detection of joints in the pipeline. The spectra may be stored in their entirety, or selected parts only may be stored, or they may be processed prior to storage, for example ratios between corresponding parts of successive spectra may be determined, and stored. Data may be selected for storage either continuously for given regions of the pipeline, or when a departure from a norm occurs. The norm may be determined either by means of the temporary storage and averaging of data from one or more previous sections of pipeline, or the norm may be present before the test vehicle is launched into the pipeline.

The chassis of the test vehicle may be adapted to carry two detectors for the said ionising radiation positioned at different axial distances from the neutron source, or a single detector at a predetermined axial distance from the neutron source.

Preferably a plurality of individual detectors is disposed symmetrically so as to observe the inner surface of the wall of the pipeline radially so as to provide information as to the azimuth of the measured ionising radiation.

Also, the means for recording the measuring intensities of the ionising radiation may be adapted to carry out the determination of the rate of fall-off of the neutron flux with axial distance from the neutron source and record this parameter. The said means may be further adapted to record the said parameter only when it departs from a predetermined value known to be indicative of a satisfactory coated and buried pipeline, together with appropriate position data when such a departure from the specified value of the parameter occurs.

According to the invention in another aspect, the method comprises the operations of continuously determining the spectrum of $\gamma$-rays within the pipeline arising from the said nuclear reactions, temporarily storing the $\gamma$-ray spectrum determined at a given instant, comparing the stored $\gamma$-ray spectrum with one determined at a later instant, the stored $\gamma$-ray spectrum being continuously up-dated, and recording differences between the $\gamma$-ray spectra above a predetermined level together with data representative of the position of the vehicle along the pipeline at which the recorded differences in the $\gamma$-ray spectra within the pipeline occur.

Also according to the invention in this aspect, the chassis of the test vehicle includes means for determining the spectra of $\gamma$-radiation within the pipeline arising from the said nuclear reactions, means for temporarily storing the $\gamma$-ray spectra determined at a given instant, means for continuously up-dating the $\gamma$-ray spectra stored in the temporary store, means for comparing the stored $\gamma$-ray spectrum with one determined at a later instant, means for determining the position of the vehicle along the pipeline, a data recorder for recording $\gamma$-ray spectra and position data, and means for activating the data recorder whenever the difference between a temporary stored $\gamma$-ray spectrum and a later determined $\gamma$-ray spectrum exceeds a predetermined value.

According to the invention in another aspect, the energy spectrum of the ionising radiation is measured, together with position data, and stored for analysis later. Again, this may be done at one or two axial locations.

The ionising radiation may be $\gamma$-rays or thermal neutrons returning from the media surrounding the pipeline.

A suitable neutron source is a quantity of Californium −252, and suitable $\gamma$-ray detectors are NaI (T1) scintillation detectors.

The invention will now be described by way of example, with reference to the accompanying drawings, in which:

FIG. 5 shows a block circuit diagram of alternative instrumentation for use with the test vehicle of FIG. 3.

Figure 1:
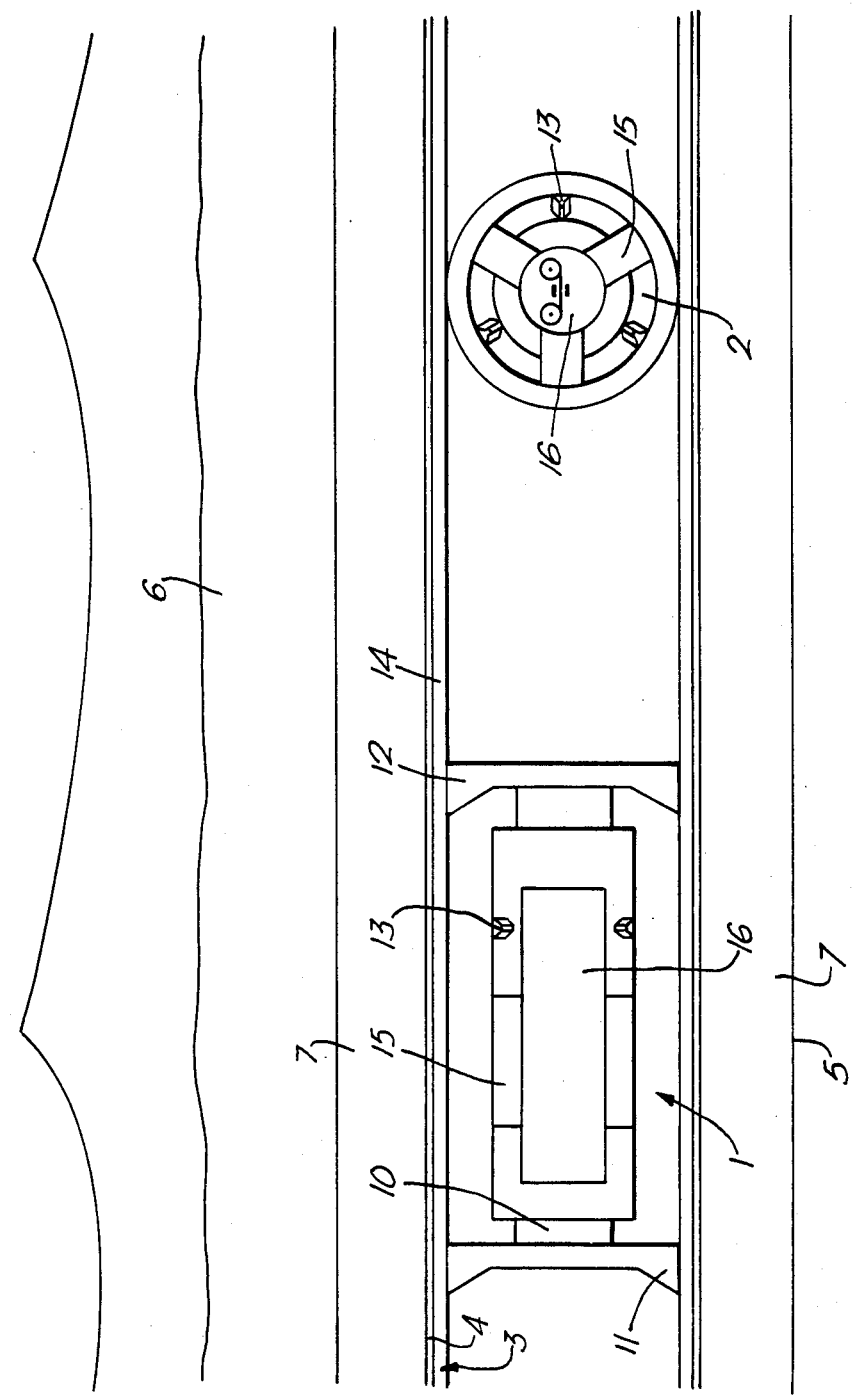
FIG. 1 shows a schematic diagram of a portion of a marine pipeline in which there are two types of test vehicle embodying the invention in one aspect.

Referring to FIG. 1, two pipeline test vehicles are shown. The first test vehicle, designed by the reference numeral 1, is based upon a pig such as those which are used for separating different fluids travelling along a pipeline, or for cleaning the inside of a pipeline. The second test vehicle, designated by the reference numeral 2, is based on an inflated rubber sphere. In each case the test vehicle is designed to be transmitted through the pipeline by the fluid which is flowing through it.

The test vehicles 1 and 2 are shown within a length of steel pipeline 3 which is clad with a layer of bitumen 4, which can include some fibrous material such as felt or woven glass fibre as a strengthening agent. The pipeline 3 is laid in a trench 5 in the sea bed 6. The pipeline 3 is embedded in concrete 7 prior to back-filling of the trench 5.

The test vehicle 1 consists of a cylindrical chassis 10 which is supported between two pistons, 11 and 12 which are of a fit within the pipeline 3 such that the test vehicle 1 can be propelled along the pipeline 3 by a fluid flowing through the pipeline 3. At the leading end of the chassis 10 of the test vehicle 1 are six separate Californium-252 neutron sources 13. The neutron sources 13 are arranged to irradiate evenly the wall 14 of the pipeline 3. The neutron sources 13 are mounted within, and shielded by, the structure of the chassis 10 of the test vehicle 1. Behind the neutron sources 13 are six NaI (T1) scintillation $\gamma$-ray detectors 15. The scintillation $\gamma$-ray detectors 15 are spaced regularly around the chassis 10 of the test vehicle 1 so that they together observe the whole of the inner surface of the wall 14 of the pipeline 3. The output signals from the scintillation $\gamma$-ray detectors 15 are fed into a battery-powered electronics and recording module 16 to which signals representative of the position of the test vehicles along the length of the pipeline also are applied. The position signals can be derived either from clock pulses, on the assumption that the test vehicle 1 passes through the pipeline 3 at a constant speed, or by counting the number of joints between sections of the pipeline 3 which have been passed by the vehicle 1. These joints can be detected by the distorting effect they have on the $\gamma$-ray spectra determined by the $\gamma$-ray detectors 15. Alternatively, a mechanical or time based position data signal generator can be used. Each of the $\gamma$-ray detectors 15 has its own identified input channel to the module 16 so that the azimuths of the $\gamma$-rays can be determined.

Alternatively, the six separate neutron sources can be replaced by a single source on the centre-line of the vehicle and arranged to irradiate the wall 14 of the pipeline 3 via an aperture or apertures in shielding surrounding the central source.

The second type of test vehicle shown in FIG. 1 is based on an inflated rubber sphere which again is propelled along the pipeline 3 by the fluid flowing through it. Those components of the spherical test vehicle 2 which correspond to those of the cylindrical test vehicle 1 and have the same purpose, have the same reference numerals. The main difference is in the number of source/detector pairs. In the test vehicle 1, six are used disposed in a single plane at right angles to the longitudinal axis of the test vehicle 1. In the case of the test vehicle 2, the source/detector pairs are disposed in three dimensions so as to observe the whole solid angle of $2\pi$.

Figure 2:
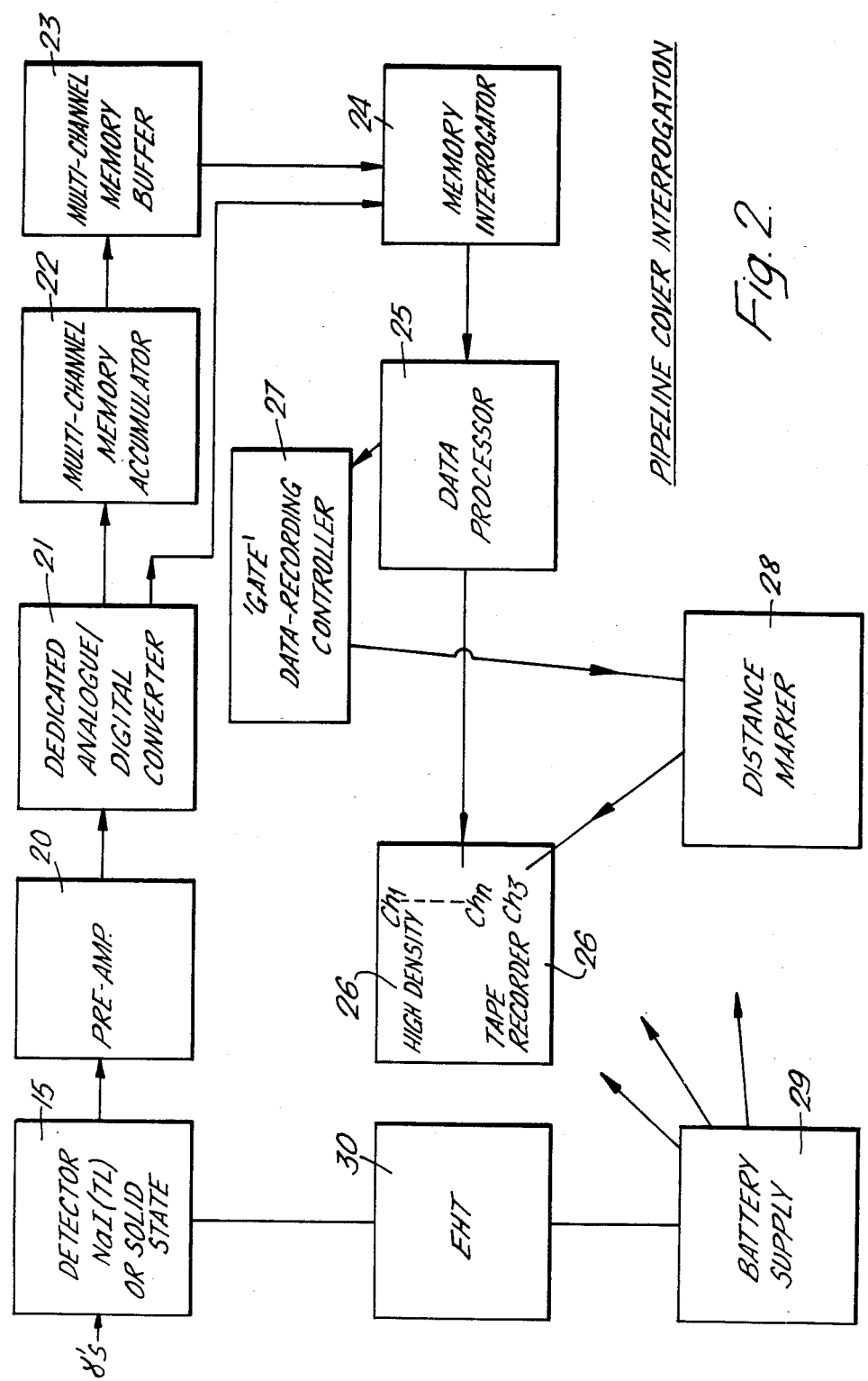
FIG. 2 shows a block circuit diagram of the instrumentation within the test vehicles of FIG. 1.

Referring to FIG. 2, there is shown a single channel of the data processing and recording system within the electronics and recording module 16. Signals representative of γ-rays falling on one of the γ-ray detectors 15 are amplified by a pre-amplifier 20 and passed to an analogue-to-digital converter 21. The output γ-ray data signals from the analogue-to-digital converter 21 are pasesd to a short term store, or memory, 22 and directly to a memory interrogator 24. After a delay of some seconds the stored γ-ray data signals are released to the memory interrogator 24 via a memory buffer 23 and replaced by fresh signals from the analogue-to-digital converter 21. This up-dating is carried on continuously. The direct and stored γ-ray signals are compared in the memory interrogator 24. If they are broadly comparable, then there is no output from the memory interrogator 24. If the two sets of γ-ray data signals differ by more than a predetermined amount, then the memory interrogator 24 produces an output signal which is applied to a data processor 25 which reduces it to a form which is suitable to be recorded on a high density tape recorder 26. The data processor 25 also produces a control signal which actuates a controller 27. The controller 27 operates so as to switch on the tape recorder 26 only when there is an output from the data processor 25, and also causes position marking signals from a distance marker 28 to be applied to the tape recorder 26.

In practice, all the circuit components from the analogue to digital converter 21 onwards are multi-channel, there being a channel for each γ-ray detector 15. The detectors each have a pre-amplifier 20.

The electronics and recording module 16 is powered by battery 29 and a high voltage generator 30.

The distance marker 28 counts the number of pipeline joints which have been passed by the test vehicle from the position at which it was introduced into the pipeline. The joints can be detected mechanically, or by their effect on the γ-ray spectrum within the pipeline at the positions at which they occur. Thus the position of a marked change in the cover of pipeline can be determined to within one length of pipeline.

Alternatively, if the conditions are such that the test vehicle 1 or 2 can be assumed to pass through the pipeline 3 at a constant speed, then the position marking signals can be derived from clock pulses counted by the distance marker 28.

By recording only marked changes in the γ-ray data signals corresponding to large differences in the cover of the pipeline 3, it is possible to inspect long lengths of pipeline 3 in a single run of the test vehicles 1 or 2.

Figure 3:
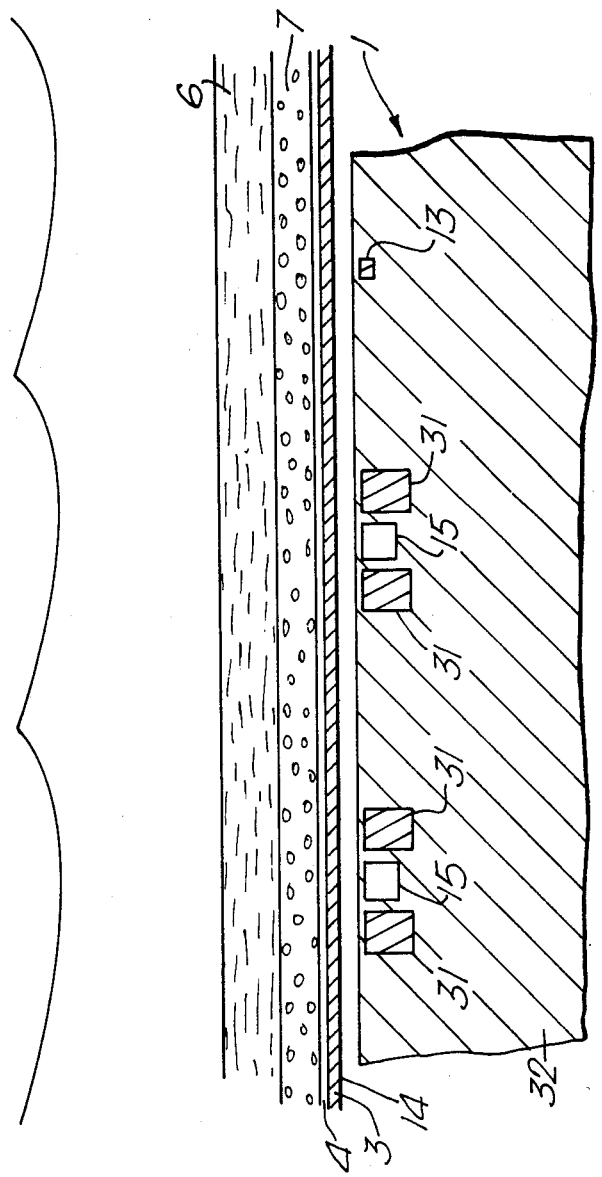
FIG. 3 shows a longitudinal section of a portion of a test vehicle embodying another aspect of the invention.

Referring to FIG. 3, in which items corresponding to the embodiment of the invention described with reference to FIG. 1 have the same reference numerals as before, the test vehicle 1 of which only a portion is shown, carries a ring of separate Californium—252 neutron sources 13 arranged so as to irradiate evenly the inner surface of the wall 14 of the pipeline 3. Behind the neutron sources 13 are two groups of NaI (T1) scintillation γ-ray detectors 15. The γ-ray detectors 15 in each group are regularly spaced around the vehicle 1 so that they together observe the whole of the inner surface of the wall 14 of the pipeline 3. Each group of γ-ray detectors 15 is sandwiched between two rings of heavy metal shielding 31 which ensure that the γ-ray detectors 15 are sensitive only to γ-rays approaching in approximately radial directions from outside the test vehicle 1. The neutron sources 13, γ-ray detectors 15, and shielding rings 31 are all placed as close to the periphery of the test vehicle 1 as is practicable, and are buried in a neutron shielding medium 32.

The neutron shielding material 32 must be such that it does not generate capture γ-rays or inelastic scattering γ-rays. A suitable material is a boron-loaded plastics material. The remainder of the test vehicle is similar to those already described, and will not be described further.

Figure 4:
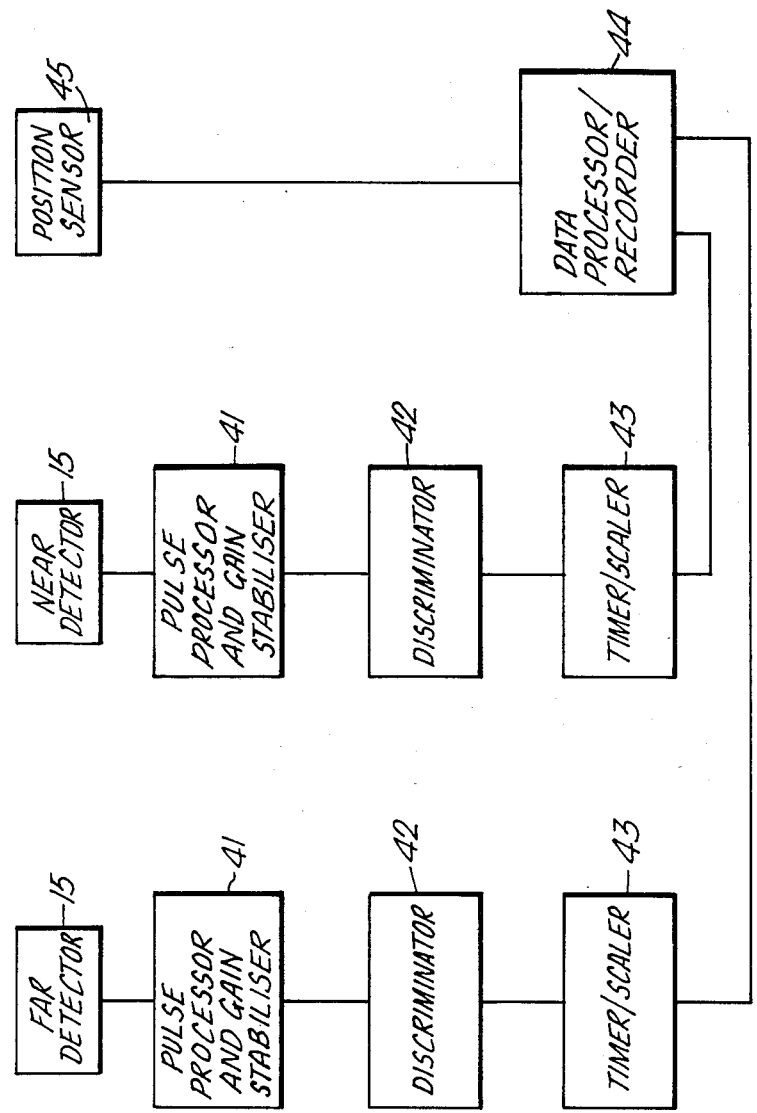
FIG. 4 shows a block circuit diagram of instrumentation carried within the test vehicle of FIG. 3.

The data processing system however, is different, and is shown in FIG. 4. The system is shown as if only single γ-ray detectors 15 are used. In practice, either each detector 15 can have its own associated data processing channel, or they can be multi-plexed into a single channel for each group of γ-ray detectors 15, or indeed, into a single channel for all of the γ-ray detectors 15. Referring to the drawing, each γ-ray detector 15 is associated with a pulse processor and gain stabiliser circuit 41 which in effect, standardises each γ-ray detector 15 against the others so that for a given γ-ray intensity each of the γ-ray detectors 15 produces the same output signal. The output signals from the pulse processor and gain stabiliser circuit 41 are applied to discriminators 42 which are arranged to intercept signals from the pulse processor and gain stabiliser circuits 41 which correspond to γ-rays having energies below 2.5 Mev which arise from hydrogen. The signals from the discriminators 42 are applied to timer scaler circuits 43 which reduce them to a standard form and pass them in sequence to a data recorder 44. Data from a position sensor 45 also are applied to the data recorder 44. The position data can be generated as previously described, or by means of an odometer operated by wheels which bear on the inner surface of the wall 14 of the pipeline 3. The data recorder 44 either can just record raw data applied to it, or it can be made to process the data. As before, the data processor/recorder 44 can be made to activate the data recording portion only when the desired parameter departs sufficiently from a value which is known to correspond to a properly covered pipeline.

It is necessary to discriminate against γ-rays from hydrogen because, as this material surrounds the pipeline 3 out to large distances form the γ-ray detectors 15, the intensity of these γ-rays is insensitive to the presence or absence of the pipeline cover material 6.

If desired, thermal neutrons rather than γ-rays can be used as the ionising radiation. In this case, the detectors can be 3 He proportional counters. Such detectors do not have the same severe gain stabilisation requirements as do scintillation detectors. Hence the data processing/recording system can be simplified by omitting these components, as is shown in FIG. 5.

A disadvantage of using thermal neutrons as the ionising radiation is that the sensitivity is reduced to about half that achieved with γ-rays.

We claim:

1. A method of determining the integrity of material in covering or supporting relationship with a buried pipeline from recorded data obtained from a single run of a pig through said pipeline, said pig comprising source means which emits output radiation and said run of said pig causing interactions between said output radiation and said material all around said pipeline, which interactions produce ionizing radiation directed toward said pig, said pig further comprising shield material, a longitudinal axis, and detectors arranged around said axis and producing first data in response to said ionizing radiation, said detectors being shielded by said shield material so that each of said detectors responds primarily to said ionizing radiation from those of said interactions arising anywhere in a respective one of a number of view fields each extending part way around said pipeline, said first data from each said detector being representative of said ionizing radiation from said interactions in said respective field, said method further comprising, as said pig advances through said pipeline, recording in said pig for each said detector respective data to produce said recorded data, and recording in said pig second data representative of the position of said pig along said pipeline.

2. A method according to claim 1 comprising forming from parts of successive energy spectras of said ionizing radiation for each detector successive ratios indicative for each said respective view field of the presence or absence of said material.

3. A method according to claim 1 wherein said source means comprises a single source located on said central longitudinal axis.

4. A method according to claim 1 wherein said source means comprises several sources arranged around said central longitudinal axis.

5. A method according to claim 1 wherein said detectors comprise two arrays thereof at different distances from said source means.

6. A means according to claim 1 wherein said source means comprises neutron source means and said ionizing radiation comprises gamma radiation.

7. A pipeline pig for use in determining the integrity of material in covering or supporting relationship with a buried pipeline, said pig having a central longitudinal axis and comprising source means to emit output radiation having interactions with said material all around said pipeline, which interactions produce ionizing radiation directed toward said pig, said pig further comprising shield material and detectors arranged around said axis and producing first data in response to said ionizing radiation, said shield material being arranged to shield said detectors from direct irradiation by said output radiation, said shield material being arranged to ensure that each of said detectors responds primarily to said ionizing radiation from those of said interactions arising anywhere in a respective one of a number of view fields each extending part way around said pipeline, said first data from each said detector being representative of said ionizing radiation from said interactions in said respective view field, said pig further comprising means which produces second data representative of the position of said pig along said pipeline, and recorder means which records said first and second data.

8. A pig according to claim 7 further comprising means for processing said first data so as to produce for each detector processed data representative of successive energy spectra of said ionizing radiation.

9. A pig according to claim 7 wherein said source means comprises sources each containing a radioactive isotope which continually emits said output radiation, said sources being arranged around said axis, and said shield material defining opening means allowing said output radiation to radiate from said sources along paths avoiding said detectors.

10. A pig according to claim 9 wherein said source meams comprises neutron source means and said ionizing radiation comprises gamma radiation.

11. A pig according to claim 7 wherein said source means comprises neutron source means and said ionizing radiation comprises gamma radiation.

* * * * *